(12) United States Patent
Lowe et al.

(10) Patent No.: US 7,762,403 B2
(45) Date of Patent: *Jul. 27, 2010

(54) FLEXIBLE TUBE FOR CARTRIDGE FILTER

(75) Inventors: Brian J. Lowe, Zimmerman, MN (US); Alan D. Eskuri, Hanover, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/260,300

(22) Filed: Oct. 29, 2008

(65) Prior Publication Data

US 2009/0054907 A1 Feb. 26, 2009

Related U.S. Application Data

(63) Continuation of application No. 11/040,631, filed on Jan. 21, 2005, now Pat. No. 7,459,080, which is a continuation of application No. 10/373,482, filed on Feb. 24, 2003, now Pat. No. 6,878,291.

(51) Int. Cl.
*B01D 33/01* (2006.01)

(52) U.S. Cl. ............... 210/359; 210/459; 210/483; 210/497.01; 606/108; 606/200

(58) Field of Classification Search ............ 210/437, 210/438, 459, 460, 359, 483–485, 497.01, 210/767, 321.6, 321.67, 321.87, 232, 497.1; 606/200, 108, 127, 159; 604/96.01, 102.01, 604/103.01, 500, 891.1

See application file for complete search history.

(56) References Cited

U.S. PATENT DOCUMENTS 3,278,991 A 10/1966 Peternell et al.
3,472,230 A 10/1969 Fogarty
3,952,747 A 4/1976 Kimmel, Jr.
3,996,938 A 12/1976 Clark, III
4,046,150 A 9/1977 Schwartz et al.
4,373,009 A 2/1983 Winn
4,425,908 A 1/1984 Simon
4,494,531 A 1/1985 Gianturco (Continued)

FOREIGN PATENT DOCUMENTS

DE 2821048 7/1980

(Continued)

OTHER PUBLICATIONS

"Endovascular Grafts, Stents Drive Interventional Radiology Growth," Cardiovascular Device Update, 2(3):1-12 (Mar. 1996).

(Continued)

*Primary Examiner*—Joseph W Drodge
(74) *Attorney, Agent, or Firm*—Crompton, Seager & Tufte LLC

(57) ABSTRACT

Embolic protection filtering devices and methods of making and using the same. The present invention may include an embolic protection filtering device including a filter cartridge that is slidable over medical devices, for example, guidewires. The filter cartridge may have a filter coupled thereto and may have desirable flexibility and trackability characteristics.

10 Claims, 4 Drawing Sheets

U.S. PATENT DOCUMENTS

| | | |
|---|---|---|
| 4,590,938 A | 5/1986 | Segura et al. |
| 4,619,246 A | 10/1986 | Molgaard-Nielsen et al. |
| 4,643,184 A | 2/1987 | Mobin-Uddin |
| 4,650,466 A | 3/1987 | Luther |
| 4,688,553 A | 8/1987 | Metals |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,832,055 A | 5/1989 | Palestrant |
| 4,842,579 A | 6/1989 | Shiber |
| 4,873,978 A | 10/1989 | Ginsburg |
| 4,874,373 A | 10/1989 | Luther et al. |
| 4,917,085 A * | 4/1990 | Smith ..................... 606/159 |
| 4,921,478 A | 5/1990 | Solano et al. |
| 4,921,484 A | 5/1990 | Hillstead |
| 4,926,858 A | 5/1990 | Gifford, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |
| 5,108,419 A | 4/1992 | Reger et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,329,942 A | 7/1994 | Gunther et al. |
| 5,330,484 A | 7/1994 | Gunther |
| 5,354,310 A | 10/1994 | Garnie et al. |
| 5,376,100 A | 12/1994 | Lefebvre |
| 5,421,832 A | 6/1995 | Lefebvre |
| 5,423,742 A | 6/1995 | Theron |
| 5,423,885 A | 6/1995 | Williams |
| 5,449,372 A | 9/1995 | Schmaltz et al. |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Bouewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassel et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,976,172 A | 11/1999 | Homsma et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,013,093 A | 1/2000 | Nott et al. |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,156,046 A | 12/2000 | Passafaro et al. |
| 6,159,195 A | 12/2000 | Ha et al. |
| 6,165,200 A | 12/2000 | Tsugita et al. |
| 6,168,579 B1 | 1/2001 | Tsugita |
| 6,171,327 B1 * | 1/2001 | Daniel et al. ................ 606/200 |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,336,934 B1 | 1/2002 | Gilson et al. |
| 6,340,364 B2 | 1/2002 | Kanesaka |
| 6,344,049 B1 | 2/2002 | Levinson et al. |
| 6,346,116 B1 | 2/2002 | Brooks et al. |
| 6,355,051 B1 | 3/2002 | Sisskind et al. |
| 6,361,546 B1 | 3/2002 | Khosravi |
| 6,371,969 B1 | 4/2002 | Tsugita et al. |
| 6,371,970 B1 | 4/2002 | Khosravi et al. |
| 6,371,971 B1 | 4/2002 | Tsugita et al. |

| | | | |
|---|---|---|---|
| 6,383,206 B1 | 5/2002 | Gillick et al. | |
| 6,428,559 B1 | 8/2002 | Johnson | |
| 6,432,122 B1 | 8/2002 | Gilson et al. | |
| 6,443,926 B1 | 9/2002 | Kletschka | |
| 6,443,971 B1 | 9/2002 | Boylan et al. | |
| 6,443,972 B1 | 9/2002 | Bosma et al. | |
| 6,468,291 B2 | 10/2002 | Bates et al. | |
| 6,485,456 B1 | 11/2002 | Kletschka | |
| 6,511,462 B1 | 1/2003 | Itou et al. | |
| 6,511,496 B1 | 1/2003 | Hurter et al. | |
| 6,511,503 B1 | 1/2003 | Burkett et al. | |
| 6,596,011 B2 | 7/2003 | Johnson et al. | |
| 6,616,680 B1 | 9/2003 | Thielen | |
| 6,726,702 B2 | 4/2004 | Khosravi | |
| 6,878,291 B2 * | 4/2005 | Lowe et al. | 210/767 |
| 7,459,080 B2 * | 12/2008 | Lowe et al. | 606/200 |
| 2002/0090389 A1 | 7/2002 | Humes et al. | |
| 2003/0045897 A1 | 3/2003 | Hunter et al. | |
| 2003/0060843 A1 | 3/2003 | Boucher | |
| 2003/0130684 A1 | 7/2003 | Brady et al. | |
| 2003/0176889 A1 | 9/2003 | Boyle et al. | |
| 2004/0082967 A1 | 4/2004 | Broome et al. | |
| 2004/0127933 A1 * | 7/2004 | Demond et al. | 606/200 |

FOREIGN PATENT DOCUMENTS

| | | |
|---|---|---|
| DE | 3417738 | 11/1985 |
| DE | 4030998 | 4/1991 |
| DE | 19916162 | 10/2000 |
| EP | 0200688 | 11/1986 |
| EP | 0293605 | 12/1988 |
| EP | 0411118 | 2/1991 |
| EP | 0427429 | 5/1991 |
| EP | 0437121 | 7/1991 |
| EP | 0472334 | 2/1992 |
| EP | 0472368 | 2/1992 |
| EP | 0533511 | 3/1993 |
| EP | 0655228 | 11/1994 |
| EP | 0686379 | 6/1995 |
| EP | 0696447 | 2/1996 |
| EP | 0737450 | 10/1996 |
| EP | 0743046 | 11/1996 |
| EP | 0759287 | 2/1997 |
| EP | 0771549 | 5/1997 |
| EP | 0784988 | 7/1997 |
| EP | 0852132 | 7/1998 |
| EP | 0934729 | 8/1999 |
| EP | 1127556 A2 | 8/2001 |
| FR | 2580504 | 10/1986 |
| FR | 2643250 | 8/1990 |
| FR | 2666980 | 3/1992 |
| FR | 2694687 | 8/1992 |
| FR | 2768326 | 3/1999 |
| GB | 2020557 | 1/1983 |
| JP | 8-187294 | 7/1996 |
| SU | 764684 | 9/1980 |
| WO | 8809683 | 12/1988 |
| WO | 9203097 | 3/1992 |
| WO | 9414389 | 7/1994 |
| WO | 9424946 | 11/1994 |
| WO | 9601591 | 1/1996 |
| WO | 9610375 | 4/1996 |
| WO | 9619941 | 7/1996 |
| WO | 9623441 | 8/1996 |
| WO | 9633677 | 10/1996 |
| WO | 9717100 | 5/1997 |
| WO | 9727808 | 8/1997 |
| WO | 9742879 | 11/1997 |
| WO | 9802084 | 1/1998 |
| WO | 9802112 | 1/1998 |
| WO | 9823322 | 6/1998 |
| WO | 9833443 | 8/1998 |
| WO | 9834673 | 8/1998 |
| WO | 9836786 | 8/1998 |
| WO | 9838920 | 9/1998 |
| WO | 9838929 | 9/1998 |
| WO | 9839046 | 9/1998 |
| WO | 9839053 | 9/1998 |
| WO | 9846297 | 10/1998 |
| WO | 9847447 | 10/1998 |
| WO | 9849952 | 11/1998 |
| WO | 9850103 | 11/1998 |
| WO | 9851237 | 11/1998 |
| WO | 9855175 | 12/1998 |
| WO | 9909895 | 3/1999 |
| WO | 9922673 | 5/1999 |
| WO | 9923976 | 5/1999 |
| WO | 9925252 | 5/1999 |
| WO | 9930766 | 6/1999 |
| WO | 9940964 | 8/1999 |
| WO | 9942059 | 8/1999 |
| WO | 9944510 | 9/1999 |
| WO | 9944542 | 9/1999 |
| WO | 9955236 | 11/1999 |
| WO | 9958068 | 11/1999 |
| WO | 0007521 | 2/2000 |
| WO | 0007655 | 2/2000 |
| WO | 0009054 | 2/2000 |
| WO | 0016705 | 3/2000 |
| WO | 0049970 | 8/2000 |
| WO | 0053120 | 9/2000 |
| WO | 0058068 | 10/2000 |
| WO | 0067664 | 11/2000 |
| WO | 0067665 | 11/2000 |
| WO | 0067666 | 11/2000 |
| WO | 0067668 | 11/2000 |
| WO | 0067669 | 11/2000 |
| WO | 0105462 | 1/2001 |
| WO | 0108595 | 2/2001 |
| WO | 0108596 | 2/2001 |
| WO | 0108742 | 2/2001 |
| WO | 0108743 | 2/2001 |
| WO | 0110320 | 2/2001 |
| WO | 0115629 | 3/2001 |
| WO | 0121077 | 3/2001 |
| WO | 0121100 | 3/2001 |
| WO | 0126726 | 4/2001 |
| WO | 0135857 | 5/2001 |
| WO | 0143662 | 6/2001 |
| WO | 0147579 | 7/2001 |
| WO | 0149208 | 7/2001 |
| WO | 0149209 | 7/2001 |
| WO | 0149215 | 7/2001 |
| WO | 0149355 | 7/2001 |
| WO | 0152768 | 7/2001 |
| WO | 0158382 | 8/2001 |
| WO | 0160442 | 8/2001 |
| WO | 0167989 | 9/2001 |
| WO | 0170326 | 9/2001 |
| WO | 0172205 | 10/2001 |
| WO | 0187183 | 11/2001 |
| WO | 0189413 | 11/2001 |
| WO | 0191824 | 12/2001 |

OTHER PUBLICATIONS

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," AJR, 141:601-604 (Sep. 1983).

Cragg, Andrew et al., "Nonsurgical Placement of Arterial Endoprosthesis: A New Technique Using Nitinol Wire," AJR, pp. 261-263 (Apr. 1983).

Diethrich et al., "Percutaneous Techniques for Endoluminal Carotid Interventions," J. Endovasc. Surg., 3:182-202 (1996).

Fadali, A. Moneim, "A filtering device for the prevention of particulate embolization during the course of cardiac surgery," Surgery, 64(3):634-639 (Sep. 1968).

Haissaguerre et al., "Spontaneous Initiation of Atrial Fibrillation by Ectopic Beats Originating in the Pulmonary Veins," The New England Journal of Medicine, 339(10):659-666 (Sep. 1988).

Jordan, Jr. et al., "Microemboli Detected by Transcranial Doppler Monitoring . . . ," Cardiovascular Surgery, 7(1)33-38 (Jan. 1999).

Lesh, "Can Catheter Ablation Cure Atrial Fibrillation?" ACC Current Journal Review, pp. 38-40 (Sep./Oct. 1997).

Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplasty . . . ," American Heart Journal, 125(2 Pt 1):362-366 (Feb. 1993).

Mazur et al., "Directional Atherectomy with the Omnicath™: A Unique New Catheter System," Catheterization and Cardiovascular Diagnosis, 31:17-84 (1994).

Moussa, MD, Issaam "Stents Don't Require Systemic Anticoagulation . . . But the Technique (and Results) Must be Optimal," Journal of Invasive Cardiol., 8(E):3E-7E, (1996).

Nakanishi et al., "Catheter Intervention to Venous System Using Expandable Metallic Stents," Rinsho Kyobu Geka, 14 (2):English Abstract Only (Apr. 1994).

Onal et al., "Primary Stenting for Complex Atherosclerotic Plaques in Aortic and Iliac Stenoses," Cardiovascular & Interventional Radiology, 21(5):386-392 (1998).

Theron et al., "New Triple Coaxial Catheter System for Carotid Angioplasty with Cerebral Protection," American Journal of Neuroradiology, 11:869-874 (1990).

Tunick et al., "Protruding atherosclerotic plaque in the aortic archo f patients with systemic embolization: A new finding seen by transesophageal echocardiography," American Heart Journal 120(3):658-660 (Sep. 1990).

Waksman et al., "Distal Embolization is Common After Directional Atherectomy . . . ," American Heart Journal, 129 (3):430-435 (1995).

Wholey, Mark H. et al., PTA and Stents in the Treatment of Extracranial Circulation, The Journal of Invasive Cardiology, 8(E):25E-30E (1996).

* cited by examiner

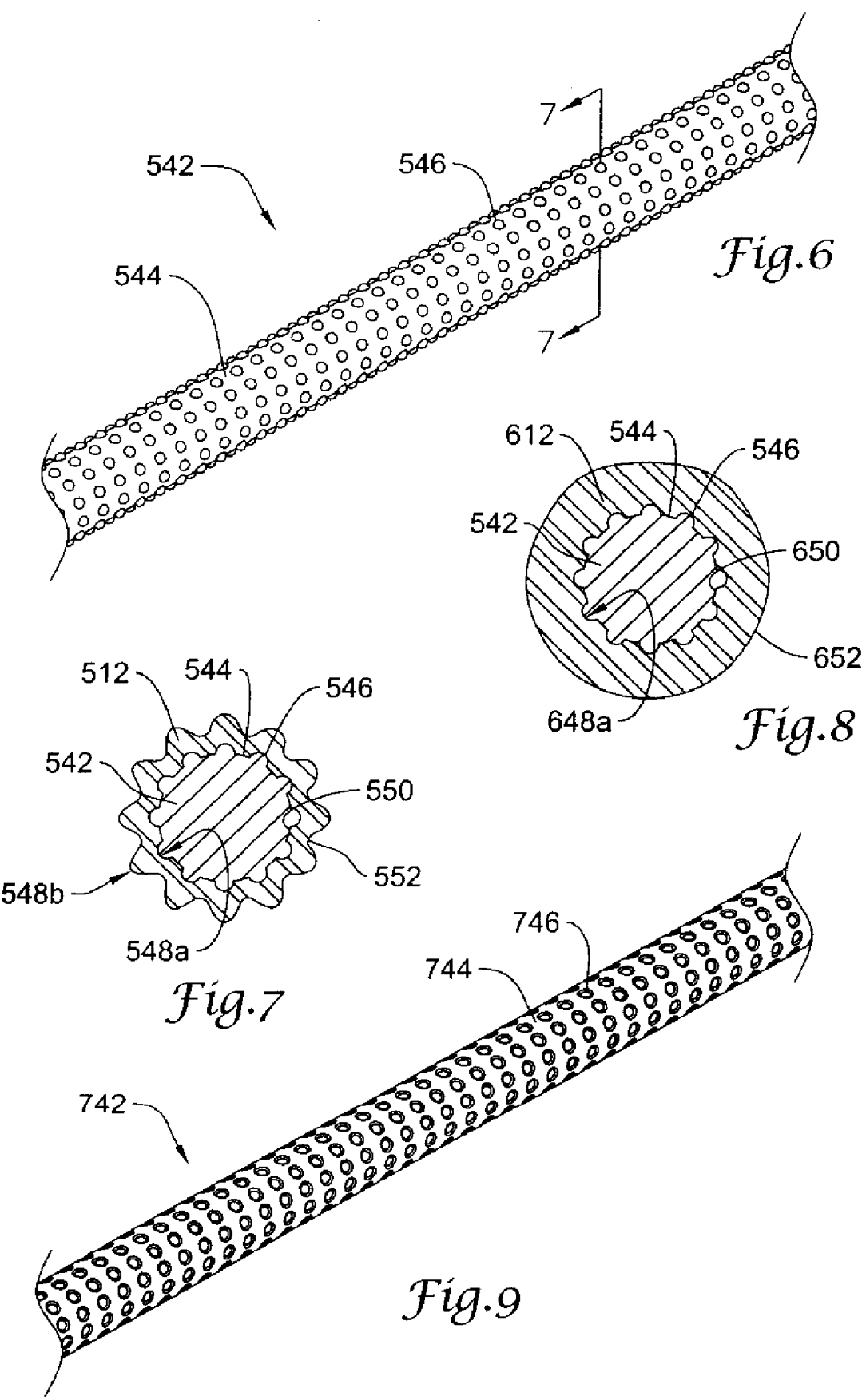

FLEXIBLE TUBE FOR CARTRIDGE FILTER

RELATED APPLICATIONS

This application is a continuation of U.S. application Ser. No. 11/040,631 filed Jan. 21, 2005, now U.S. Pat. No. 7,459,080, which is a continuation of U.S. application Ser. No. 10/373,482 filed Feb. 24, 2003, now U.S. Pat. No. 6,878,291.

FIELD OF THE INVENTION

The present invention pertains to embolic protection filters. More particularly, the present invention pertains to filters coupled to a shaft having desirable flexibility and trackability characteristics.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

BRIEF SUMMARY

The present invention pertains to embolic protection filtering devices. In at least some embodiments, the filtering device may include a filter cartridge having a filter coupled thereto. The filter cartridge may be configured to be slidable over a medical device, for example a guidewire, and may have desirable flexibility, trackability, and other features and/or characteristics as described in more detail below.

BRIEF DESCRIPTION OF THE DRAWINGS

FIG. 6 is a perspective view of an example mandrel;

FIG. 7 is a cross-sectional view taken through line 7-7;

FIG. 8 is an alternative cross-sectional view taken through line 7-7; and

FIG. 9 is a perspective view of another example mandrel.

DETAILED DESCRIPTION

Figure 1:
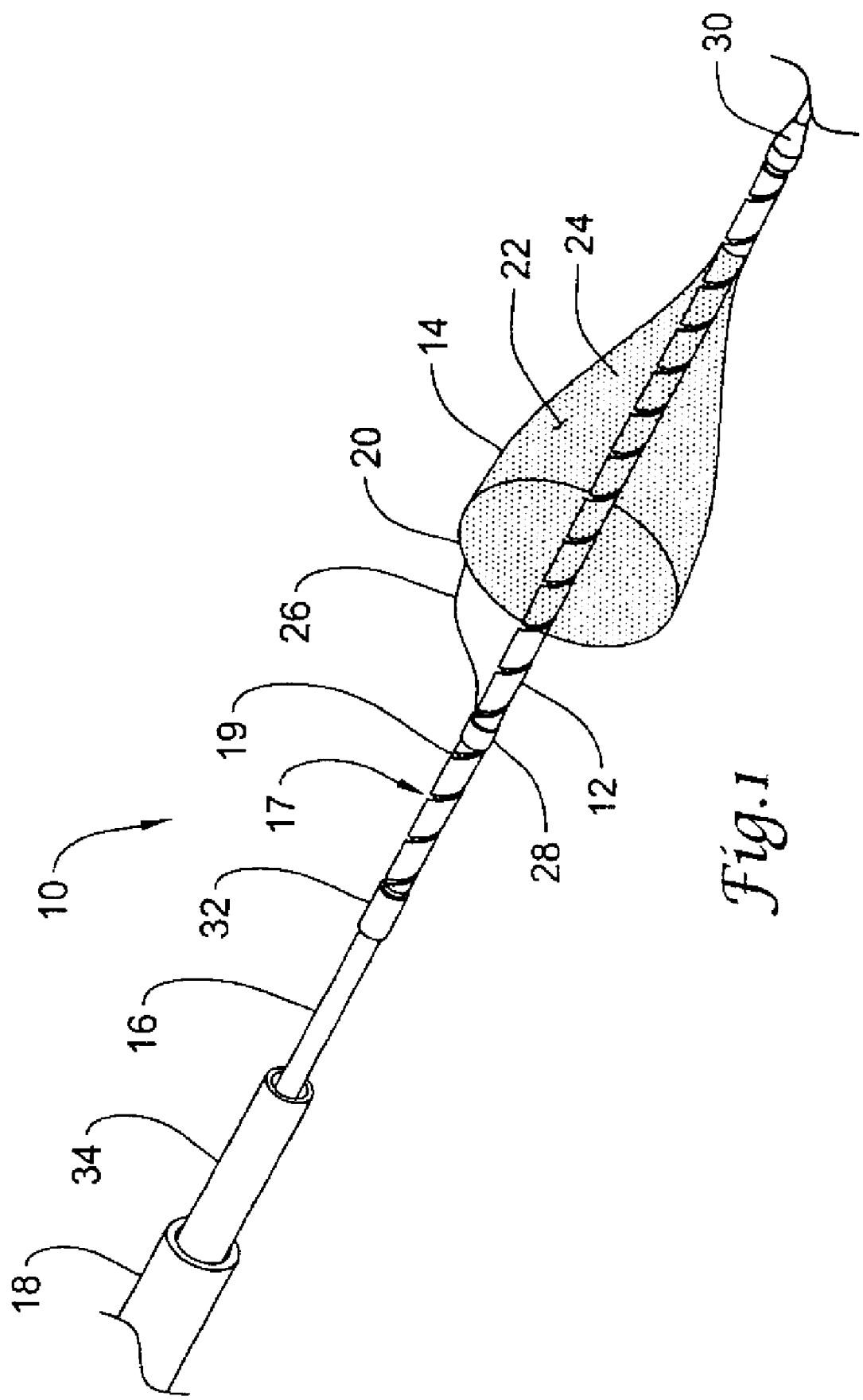
FIG. 1 is a perspective view of an example embolic protection filtering device.

The following description should be read with reference to the drawings wherein like reference numerals indicate like elements throughout the several views. The detailed description and drawings illustrate example embodiments of the claimed invention.

FIG. 1 illustrates an example embolic protection filtering device 10. Device 10 may include a tubular filter cartridge 12 having a filter 14 coupled thereto. Filter cartridge 12 may have desirable flexibility, trackability, and/or other characteristics that allow it to be exchanged over other medical devices such as a guidewire 16 (as shown in FIG. 1), a catheter, and the like. Moreover, because a number of the features and characteristics of filter cartridge 12 can be varied, cartridge 12 can be configured to be slidable over essentially any medical device, including virtually all commercially available guidewires and catheters.

Filter cartridge 12 may be comprised of a number of different materials including metals, metal alloys, polymers, or the like, or combinations or mixtures thereof. For example, filter cartridge 12 may be comprised of super elastic, linear elastic, and/or shape memory metals and/or metal alloys. Some examples of suitable metals and metal alloys include stainless steel, such as 304v stainless steel; such as nickel-titanium alloy, such as nitinol, nickel-chromium alloy, nickel-chromium-iron alloy, cobalt alloy, titanium and/or titanium alloys, or the like; or other suitable material.

Some examples of suitable polymers may include polytetrafluoroethylene (PTFE), ethylene tetrafluoroethylene (ETFE), fluorinated ethylene propylene (FEP), polyurethane, polypropylene (PP), polyvinylchloride (PVC), polyether-ester (for example a polyether-ester elastomer such as ARNITEL® available from DSM Engineering Plastics), polyester (for example a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene, Marlex high-density polyethylene, Marlex low-density polyethylene, linear low density polyethylene (for example REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), other suitable materials, or mixtures, combinations, or copolymers thereof. In some embodiments filter cartridge 12 can include a liquid crystal polymer (LCP) blended with other polymers to enhance torqueability. By employing selection of materials and processing techniques, thermoplastic, solvent soluble, and thermosetting variants of these and other materials can be employed to achieve the desired results.

In some embodiments, a coating, for example a lubricious, a hydrophilic, a protective, or other type of coating may be applied over portions or all of filter cartridge 12, or other portions of device 10. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

In some embodiments, filter cartridge 12 or portions thereof may be doped with, plated with, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, plastic material loaded with a radiopaque filler, and the like.

The choice for material composition may help provide filter cartridge 12 with a number of desirable characteristics. For example, material composition may provide filter cartridge 12 with desirable characteristics related to strength, flexibility, trackability, ovalization avoidance, coefficient of friction, axial compression, and the like. In addition or as an alternative to material composition, filter cartridge 12 may vary in other ways to provide filter cartridge 12 with desirable features and characteristics including those listed above. For example, the flexibility of filter cartridge 12 may vary along its length. This feature can be accomplished in a number of different manners, including changing the material composition or altering the inside and/or outside diameters of filter cartridge 12. Additionally, filter cartridge 12 may be comprised of multiple layers of materials and/or multiple sections or regions that are coupled.

In at least some embodiments, filter cartridge 12 may also include one or more notches 17 or other structural features that may, for example, provide filter cartridge 12 with desirable characteristics including those listed above. For example, FIG. 1 depicts the one or more notches 17 as defining a helical groove 19 formed in filter cartridge 12. Helical groove 19 can be formed in a number of ways. For example, groove 19 can be cut into filter cartridge 12 using known laser or other type of cutting or etching process. A number of other processes can be utilized to form groove 19. For example, filter cartridge 12 can be molded (e.g., injection molded, etc.) in a manner that defines groove 19. Alternatively, filter cartridge 12 may be comprised of a flattened ribbon that is wound into a shape that defines a tubular filter cartridge 12 having groove 19. It can be appreciated that groove 19 may be defined in a number of additional ways without departing from the spirit of the invention.

The shape, arrangement, and configuration of groove 19 may also vary. For example, groove 19 is illustrated in FIG. 1 as being an essentially regular helix extending along the length of cartridge 12. In some embodiments, however, groove 19 may vary. For example, groove 19 may extend along only portions of cartridge 12 or intermittently along sections of cartridge 12. Additionally, the pitch of groove 19 may vary. For example, the pitch of groove 19 may be relatively wide or open at some positions (e.g., near the proximal region of cartridge 12) and relatively close at others (e.g., near the distal region of cartridge 12). Moreover, the direction of groove 19 may vary. For example, groove 19 may wind about cartridge 12 in a clockwise direction, counterclockwise direction, or combinations of directions.

It can be appreciated that groove 19 in filter cartridge 12 may provide device 10 with a number of desirable features. For example, groove 19 may increase the flexibility of cartridge 12. Additionally, groove 19 may increase the trackability of cartridge 12. Trackability is understood to be the ability of one device (e.g., cartridge 12) to "track" or advance over another (e.g., guidewire 16). According to this embodiment, groove 19 may increase trackability, for example, by making cartridge 12 more adaptable or more compliant so that it may more easily track over a device (i.e., guidewire 16) that may be significantly contorted when positioned in the tortuous vasculature.

As stated above, some of the other components of device 10 may include filter 14. Filter 14 may be adapted to operate between a first generally collapsed configuration and a second generally expanded configuration for collecting debris in a body lumen. In some embodiments, filter 14 can be delivered to an appropriate intravascular location, for example "downstream" of an intravascular lesion, using an appropriate filter delivery and/or retrieval device 18. Similarly, filter 12 can be removed from the vasculature at the desired time with device 18 or another suitable device.

Filter 14 may include a filter frame 20 and a filter membrane or fabric 22 coupled to filter frame 20. Frame 20 may take the form of any one of a number of appropriate shapes and configurations. For example, frame 20 may comprise a generally circular filter mouth or loop, which may defines the primary opening for blood to travel into and be filtered by filter 14. However, essentially any appropriate shape or configuration may be utilized without departing from the spirit of the invention.

Frame 20 may be comprised of any appropriate material. For example, frame 20 may be comprised of a "self-expanding" shape-memory material such as nickel-titanium alloy (to bias filter 14 to be in the second expanded configuration). Alternatively, frame 20 may be comprised of essentially any appropriate metal, metal-alloy, polymer, combinations thereof, and the like including any of the materials described herein.

Filter membrane 22 may be comprised of any appropriate material such as a polymer and may be drilled (for example, formed by known laser techniques) or otherwise include at least one opening 24. Holes or openings 24 can be sized to allow blood flow therethrough but restrict flow of debris or emboli floating in the body lumen or cavity.

One or more struts 26 may extend between frame 20 and filter cartridge 12. In some embodiments, struts 26 can be coupled to filter cartridge 12 by a coupling 28, for example a heat-shrink tube, a crimp fitting, and the like. Alternatively, struts 26 may be coupled to filter cartridge 12 by one or more windings of struts 26 about filter cartridge 12.

As stated above, at least some embodiments of device 10 include guidewire 16, over which filter cartridge 12 may be slidably disposed. Guidewire 16 may include a distal stop 30. Distal stop 30 may define a distal-most position along guidewire 16 may be advanced to. In addition, guidewire 16 may also include a proximal stop 32. Stops 30/32 may be arranged so that filter cartridge 12 can be positioned between them. A deployment sheath 34 may also be slidably disposed over guidewire 16. Sheath 34 may be used, for example, to help advance filter cartridge 12 to the appropriate location along guidewire 16.

Although FIG. 1 illustrates filter cartridge 12 being slidably disposed over guidewire 16, the invention is not intended to be limited to use with only guidewires 16. It can be appreciated that the device could be any intravascular device or be any device designed to pass through an opening or body lumen. For example, the device may comprise a catheter (e.g., therapeutic, diagnostic, or guide catheter), endoscopic device, laproscopic device, an embolic protection device, or any other suitable device.

The use of filter cartridge 12 may include a number of steps. For example, filter cartridge 12 may be coupled to guidewire 16, for example by disposing cartridge between stops 30/32, by crimping cartridge 12 onto guidewire 16, by using other suitable mechanical connections, or by any other suitable means. In some embodiments, cartridge 12 and guidewire 16 may be coupled before guidewire 16 is advanced through a blood vessel. Alternatively, guidewire 16 may be positioned in a blood vessel and then cartridge 12 may be advanced over guidewire 16 to a suitable target location and filter 14 may be expanded. Advancing cartridge 12 over guidewire 16 may include the use of delivery sheath 18 and the expansion of filter 14 may include advancing deployment sheath 34 into contact or another suitable arrangement to expand filter 14. Sheath 18 and/or sheath 34 may be proximally retracted and another diagnostic or therapeutic device (e.g., balloon catheter, atherectomy catheter, and the like) may be advanced over guidewire 16. The expanded filter 14 may then be used to filter debris that may be generated by the therapeutic device.

Figure 2:
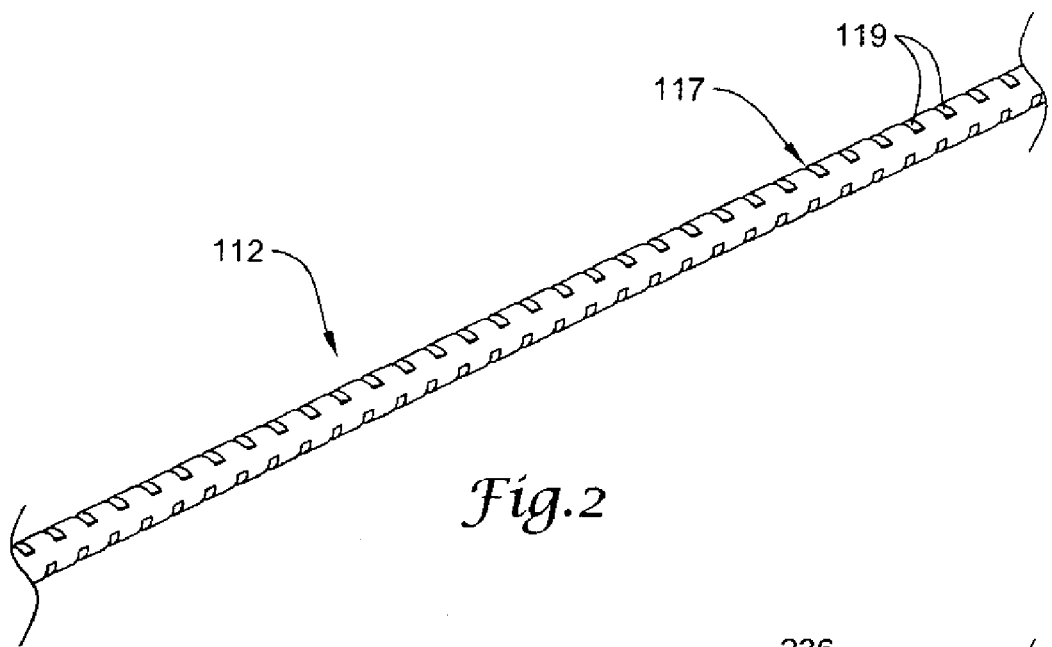
FIG. 2 is a perspective view of another example filter cartridge.

FIG. 2 is a perspective view of another example filter cartridge 112. Cartridge 112 is similar to cartridge 12, expect that the one or more notches 117 define a plurality of slots 119 within cartridge 112. Slots 119 may be formed according to any of the methods described herein or any other appropriate process. The shape, arrangement, and number of slots 119 may vary without departing from the spirit of the invention. For example, slots 119 may be generally rectangular in shape, square in shape, rounded in shape, or have any other appropriate shape. Additionally, slots 119 may be disposed at varying positions along cartridge 112 and may vary in length so as to span, for example, about 45 to about 320 degrees around the circumference of cartridge 112 or more or less, depending the desired length. In some embodiments, a bridge or other tying support (not shown) may be longitudinally disposed along cartridge 112, for example along the inside surface, to help maintain the structural integrity of cartridge 112. This structural feature may be desirable when slots 119 span larger portions of cartridge 112. Other variations for the configurations and arrangements of slots 119 may include any of the variations attributed to any of the notches and/or cartridges described herein.

Figure 3:
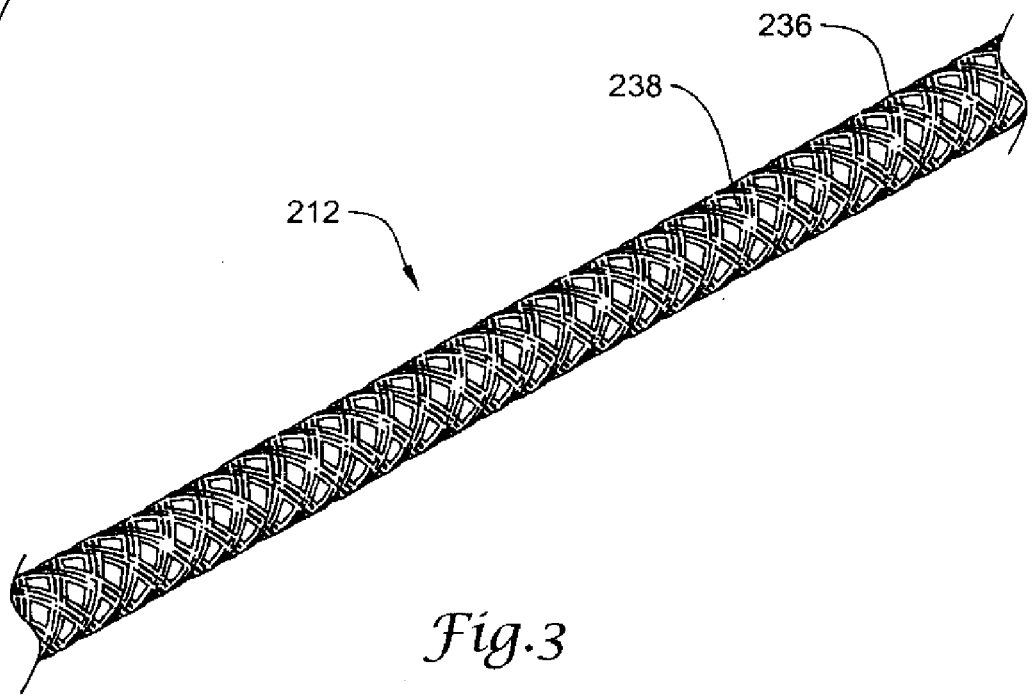
FIG. 3 is a perspective view of another example filter cartridge.

FIG. 3 is a perspective view of another example filter cartridge 212. Cartridge 212 is similar to the other cartridges disclosed herein, expect that it includes a series of fibers arranged in a braid 236. Braid 236 may be adapted and configured to provide cartridge 212 with desirable flexibility and trackability characteristics including those described above. In some embodiments, braid 236 may be disposed on the outside surface (as shown in FIG. 3) or the inside surface (not shown) of a support structure or tube 238. Alternatively, cartridge 212 may be comprised of braid 236 without the need for support tube 238. According to this embodiment, cartridge may be manufactured, for example, by disposing braid 238 on a mold or mandrel to define cartridge 212, and then disassociating the defined filter cartridge 212 from the mold.

The arrangement and configuration of braid 236 may vary. For example, braid 236 may have a uniform or regular distribution along cartridge 212. Alternatively, the pattern may be irregular or intermittent. The direction, closeness or tightness, and general shape may also vary. Moreover, additional braids or layers may be disposed on braid 236. For example, cartridge 212 may include a plurality of braids 236 disposed on each other and may include other, non-braided layers disposed therebetween.

Figure 4:
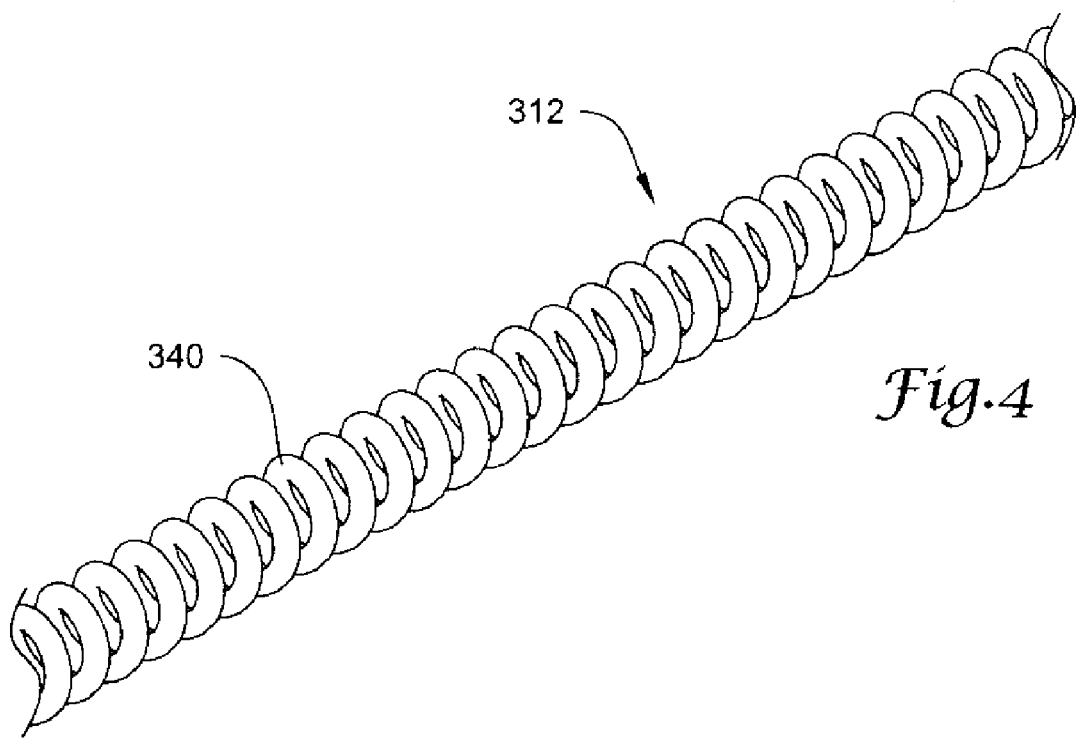
FIG. 4 is a perspective view of another example filter cartridge.

FIG. 4 is a perspective view of another example filter cartridge 312. Cartridge 312 is similar to other cartridges disclosed herein, except that it includes a coil 340. It can be appreciated that coil 340 may provide cartridge 312 with desirable flexibility characteristics. For example, including coil 340 or a similar coiled structure may increase the flexibility of cartridge 312. Additionally, coil 340 may enhance the trackability of filter cartridge 312. In some embodiments, coil 340 may comprise cartridge 312 thereby obviating the need for any support tube or structure. Other embodiments, however, may include a support structure similar to support tube 238 illustrated in FIG. 3.

Figure 5:
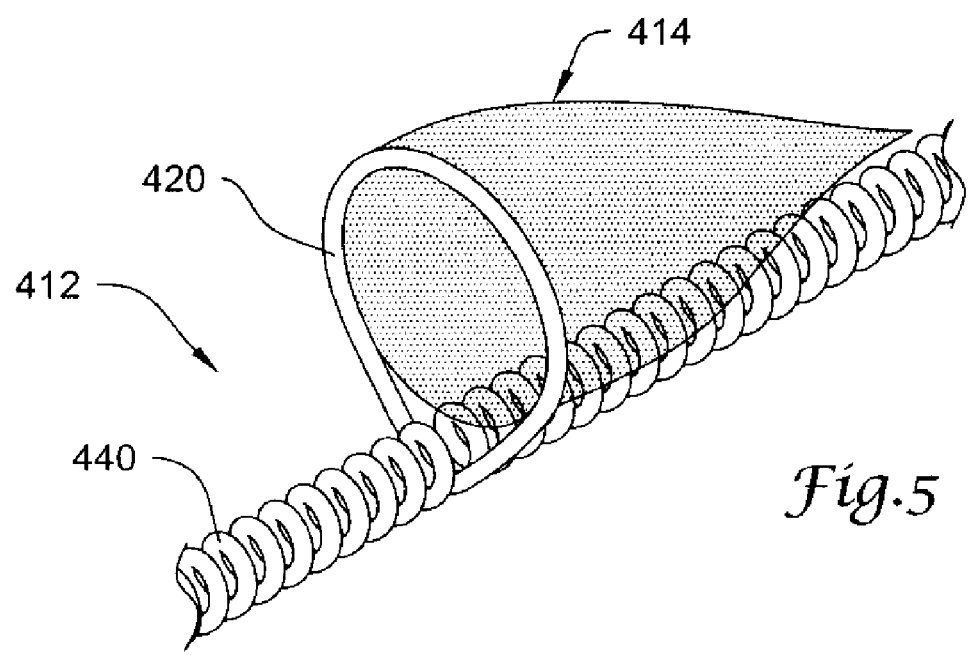
FIG. 5 is a perspective view of another example filter cartridge.

FIG. 5 is a perspective view of another example filter cartridge 412. Cartridge 412 is similar to cartridge 312, except that a portion of coil 440 is "unwound" or otherwise configured to define filter frame 420 of filter 414. According to this embodiment, cartridge 412 and filter frame 420 may be integral with one another or otherwise formed of the same structure. This structural feature may be desirable for a number of reasons. For example, cartridge 412 may cost less to manufacture by decreasing the number of separate structural elements and by decreasing some of the processing steps (e.g., attaching together separate elements).

FIG. 6 is an example mold or mandrel 542 that may be used in the manufacturing of filter cartridges, including those described herein and other embodiments. Mandrel 542 may include a base or base surface 544 and may include one or more projections 546 extending therefrom. Mandrel 542 may be comprised of any appropriate material, including those disclosed herein. In some embodiments, mandrel 542 may be comprised of a wax or other soluble substance that can be readily dissolved following the molding procedure. This feature may be desirable by enhancing the ability to release a newly molded filter cartridge from mandrel 542.

The shape, size, and arrangement of projections 546 may also vary. In some embodiments, a plurality of rounded projections 546 may be essentially uniformly distributed throughout mandrel 542. Alternatively, projections 546 may have a square or other shape and may be irregularly distributed. Additionally, a variety of shapes, sizes, and distributions may be utilized along mandrel 542.

Molding of a filter cartridge with mandrel 542 may include any of a number of known molding techniques. For example, manufacturing may include dip molding, spray molding, injection molding, and the like. These manufacturing techniques may generally include disposing a filter cartridge material (not shown) adjacent mandrel 542 so as to define a filter cartridge. The newly defined cartridge may be disassociated from mandrel 542 and the flexibility thereof may be altered. For example, the flexibility may be altered by forming one or more notches or slots therein, by forming a spiral groove therein, etc. as described above. Other manufacturing steps may include coupling a filter, for example filter 14, to the newly molded filter cartridge.

FIGS. 7 sectional and 8 illustrate cross-sectional views of mandrel 542 where example filter cartridges have been molded thereon. For example, FIG. 7 illustrates filter cartridge 512 molded on mandrel 542. According to this embodiment, the shape of cartridge 512 may include a plurality of projections 548a/b along both its inside surface 550 and its outside surface 552, respectively, that generally conform to the shape of mandrel 542. In some other embodiments, an alternative filter cartridge 612 may be molded as shown in FIG. 8. Cartridge 612 may be configured or otherwise thickened so that projections are 648a may be seen on inside surface 650, but not on outside surface 652.

Another example mandrel 742 is illustrated in FIG. 9. Mandrel 742 is essentially the same in form and function as mandrel 542, except that it includes one or more dimples 746 extending inward from a base member 744. Mandrel 742 may be used to mold filter cartridges in a manner similar to what is described above. For example, molding a filter cartridge using mandrel 742 may result in a filter cartridge with dimples similar to dimples 746.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A distal protection filter assembly, comprising:
a guidewire having a proximal end and a distal end;
a tubular member having a proximal end and a distal end, the tubular member having a notch defining a helical groove;
a distal stop on the guidewire limiting distal movement of the tubular member;
a filter having a proximal end and a distal end, the filter disposed on the tubular member, the filter proximal end slideably disposed relative to the guidewire.

2. The assembly of claim 1 wherein the groove extends along only a portion of the tubular member.

3. The assembly of claim 1 wherein the groove has a first pitch and a second pitch, wherein the second pitch is distal of the first pitch and relatively close as compared with the first pitch.

4. The assembly of claim 1 wherein the filter distal end is fixed longitudinally relative to the tubular member.

5. The assembly of claim 1 further comprising a proximal stop on the guidewire limiting proximal movement of the tubular member on the guidewire.

6. The assembly of claim 1 wherein the filter is disposed over the helical groove.

7. The assembly of claim 1 wherein the filter is disposed around the tubular member.

8. The assembly of claim 1 wherein the tubular member distal end extends distally of the filter distal end.

9. The assembly of claim I wherein the tubular member proximal end extends proximally of the filter proximal end.

10. The assembly of claim 1 wherein the notch extends both distally and proximally of the filter distal end.

* * * * *

UNITED STATES PATENT AND TRADEMARK OFFICE
CERTIFICATE OF CORRECTION

PATENT NO.        : 7,762,403 B2                              Page 1 of 1
APPLICATION NO.   : 12/260300
DATED             : July 27, 2010
INVENTOR(S)       : Brian J. Lowe and Alan D. Eskuri It is certified that error appears in the above-identified patent and that said Letters Patent is hereby corrected as shown below:

Column 8
Line 21 delete "I" and insert therefor -- 1 --.

Signed and Sealed this
Fifteenth Day of February, 2011

David J. Kappos
*Director of the United States Patent and Trademark Office*